US006238422B1

(12) United States Patent
Van Oort

(10) Patent No.: US 6,238,422 B1
(45) Date of Patent: May 29, 2001

(54) PACEMAKER SYSTEM WITH THERAPY FOR MINIMIZING RISK OF MORNING MYOCARDIAL INFARCTIONS OR ARRHYTHMIAS

(75) Inventor: Geeske Van Oort, Nieuwleusen (NL)

(73) Assignee: Medtronic, Inc., MN (US)

( * ) Notice: Subject to any disclaimer, the term of this patent is extended or adjusted under 35 U.S.C. 154(b) by 0 days.

(21) Appl. No.: 09/257,023

(22) Filed: Feb. 25, 1999

(51) Int. Cl.$^7$ .................................................. A61N 1/362
(52) U.S. Cl. .................................... 607/25; 607/9
(58) Field of Search ................... 607/9, 14, 25, 607/17

(56) References Cited

U.S. PATENT DOCUMENTS 5,065,759 * 11/1991 Begemann et al. ................... 607/25

OTHER PUBLICATIONS

Djordjevic, Milan, et al., "Circadian Variations of Heart Rate and STIM–T Interval: Adaptation for Nighttime Pacing," *PACE*, vol. 12, Nov. 1989, pp. 1757–1762.
Toivonen, Lauri et al., Electrocardiographic Repolarization During Stress From Awakening on Alarm Call, JACC, vol. 30, No. 3, Sep. 1997:774–779.
Hohnloser, Stefan H. et al., "Insights Into the Pathogenesis of Sudden Cardiac Death From Analysis of Circadian Fluctuations of Potential Triggering Factors," PACE, vol. 17, Mar. 1994, Part II, pp. 428–433.

Molnar, Janos, et al., "Diurnal Pattern of QTc Interval: How Long is Prolonged? Possible Relation to Circadian Triggers of Cardiovascular Events," JACC, vol. 27, No. 1, Jan. 1996, pp. 76–83.
Browne, Kevin F., et al., "Prolongation of the Q–T Interval in Man During Sleep," *The American Journal Cardiology*, vol. 52, pp. 55–59 Jul. 1983.

* cited by examiner

*Primary Examiner*—George R. Evanisko
(74) *Attorney, Agent, or Firm*—Thomas F. Woods; Michael J. Jaro; Harold Patton

(57) ABSTRACT

There is provided a pacemaker system having the capability of providing therapy for preventing conditions likely to lead to myocardial infarction or ventricular arrhythmia during patient morning time. Specifically, a therapy is initiated before calculated patient awakening time, for raising pacing rate slowly so as to shorten QT interval to an acceptable level relative to rate at the time of patient awakening, and specifically a level that achieves satisfactory diastolic filling time. The pre-awakening therapy pacing routine is designed to overcome normal QT prolongation which occurs during sleep state, and which is delayed after patient awakening. In the event that criteria for an acceptable diastolic filling time are not met at or after patient awakening, the pacemaker takes steps to control rate, such as ceasing synchronous pacing and limiting automatic rate response.

16 Claims, 5 Drawing Sheets

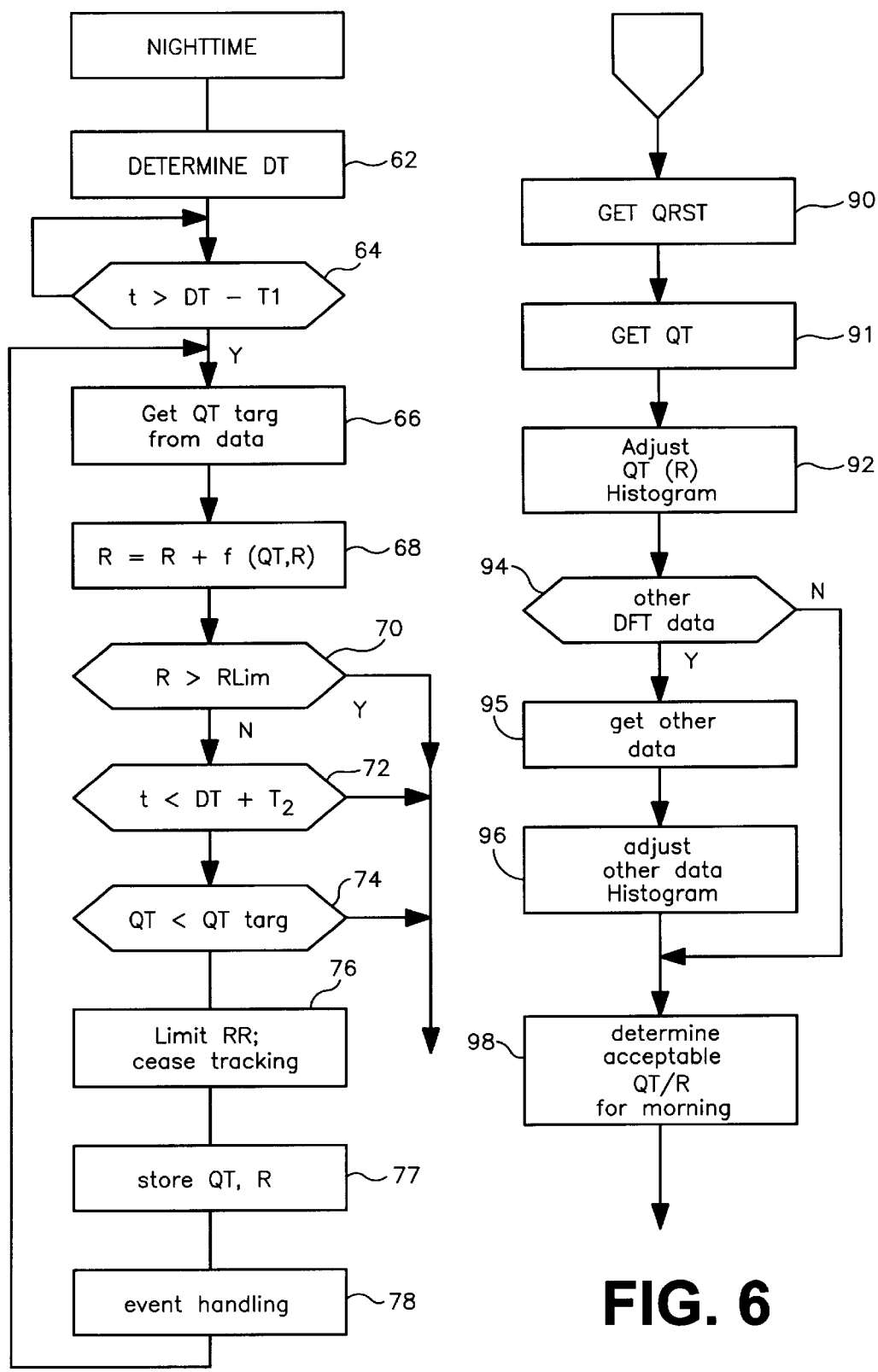

PACEMAKER SYSTEM WITH THERAPY FOR MINIMIZING RISK OF MORNING MYOCARDIAL INFARCTIONS OR ARRHYTHMIAS

FIELD OF THE INVENTION

This invention relates to cardiac pacing systems with the capability of preventing dangerous cardiac conditions, for example, implantable pacing systems that provide preventive therapy for minimizing the risk of myocardial infarction, especially during morning hours.

BACKGROUND OF THE INVENTION

Modern cardiac pacing systems have, in recent years, sought to incorporate at least some capability of detecting and dealing with various arrhythmias. For example, pacemaker designers have attempted to provide various special modes of pacing to control the effects of atrial and/or ventricular arrhythmias, particularly tachycardia and fibrillation. However, relatively little has been done to provide for preventive pacemaker therapy. For example, there is no known pacemaker therapy for preventing, or minimizing the risk of myocardia infarction (MI).

An early procedure adopted in pacemaker design for dealing with cardiac arrhythmias generally was simply to switch into an asynchronous mode, providing ordinary fixed rate asynchronous ventricular pacing. Such a response is a help, but is recognized to have limitations. Other more sophisticated response schemes have been adopted, with varying degrees of success. However, rather than simply trying to control the heart after the onset of a dangerous arrhythmia, it is to be recognized that it is preferable to anticipate when a patient may be potentially subject to a dangerous cardiac condition; and to take preventive action which aims to deal with the circumstances which give rise to the condition and thereby minimize its probability of occurrence. Relatively little work has been done in this area of preventive pacing therapies.

This invention is directed particularly toward preventing and/or responding to ventricular arrhythmias which have an increased incidence in the morning, after awakening. It is known from the literature that malignant arrhythmias, and types of acute myocardial infarctions, have a greater incidence in certain patients shortly after awakening. It is suggested that there is a circadian variability in the incidence of sudden cardiac death, with a peak in the early morning hours. See "Insights Into the Pathogenesis of Sudden Cardiac Death From Analysis of Circadian Fluctuations of Potential Triggering Factors," Hohnloser and Klingenheben, PACE, Vol. 17, March 1994, Part II, pp. 428–433. More specifically, as this reference indicates, there has been interest in exploring the relation between disturbances of ventricular repolarization, or prolonged QT interval, and sudden cardiac death. The distribution of occurences of MI over the 24-hour day reveals an increased risk shortly after the time of awakening and arising.

Other investigators likewise have discussed the potential correlation of such malignant arrhythmias and abnormal myocardial repolarization, or prolonged QT interval. It is known that the QT interval prolongs during sleep, and this prolongation extends into the arousal period. It is suggested that this QT interval prolongation may play an important role with respect to the diurnal variation of some ventricular arrhythmias. See, for example, "Prolongation of the Q-T Interval In Man During Sleep, "Browne et al,. *The America Journal of Cardiology*, July 1983, Vol. 52, pp. 55–59. See also "Electrocardiographic Repolarization During Stress From Awakening on Alarm Call," Tiovonen et al., JACC, Vol. 30, No. Sept. 3, 1997, pp. 774–779. It is known that the QT interval can vary independently of rate, and particularly that QT interval prolongs during sleep independent of any change of the RR interval. The cause of such QT variation, and the corresponding effect on cardiac rate stability, are the subject of considerable debate and analysis. However, there does appear to be a consensus that QT interval variability reaches a peak shortly after awakening, and that the time of this peak corresponds to the period of increased vulnerability to MI and ventricular tachycardias. Further, there is an inertia in adaptation of the QT interval during the period after awakening, i.e., the arousal period. By inertia it is meant that the QT interval does not directly shorten, but remains relatively prolonged, as patient heart rate increases during the time of arousal.

It is a basis of this invention that the delay in QT shortening, which results in a longer than normal QT interval after awakening, can result in an insufficient diastolic filling time for certain patients. Thus, if ventricular repolarization is extended relative to the patient's RR interval, the time available for diastolic filling is shortened. This in turn would lead to the result that insufficient blood is made available to flow through the myocardium, leaving the patient vulnerable to myocardial infarction.

SUMMARY OF THE INVENTION

It is an object of this invention to provide an implantable pacemaker device and system which obtains and utilizes data reflective of patient QT variations, and in particular circadian variations in the QRS-T signal which are indicative of reduced diastolic filling time at and shortly after patient awakening. The object of the invention is to provide an implanted device for providing preventive therapy, which device is particularly useful for patients known to have a prolonged QT interval, to be subject arrhythmias, or patients who already have myocardial ischemia or infarction. The pacemaker device of the invention provides therapy in the form of overdrive pacing to slightly increase pacing rate before the patient awakening time, so as to manage shortening of the QT interval and better provide sufficient diastolic filling time during the dangerous period following awakening.

In accordance with the above objects, the pacemaker of this invention provides for determining, each night, an expected start of daytime, or awakening of the patient. A preventive therapy routine is initiated at a predetermined time, e.g., 30 minutes, prior to awakening, suitably by slowly increasing patient rate above the underlying intrinsic rate, in order to obtain a healthy QT/R ratio for the patient by time awakening arrives. In other words, the pacemaker's pre-awakening therapy anticipates delayed QT prolongation during awakening which would otherwise occur, and programs an increase in paced heart rate so as to achieve a desired target QT or QT/R ratio, by time of awakening. In addition, the pacemaker monitors QT and R for the remainder of a predetermined morning period after awakening, and if desired QT/R criteria are not met, further responsive action is taken, e.g., inhibiting synchronous tracking of atrial signals and limiting the pacemaker rate response feature.

In a first simple version of the invention, the patient's data is either inputted by the physician or collected continuously and used to determine a target QT interval, or $QT_{targ}$, which is a measure of the minimum acceptable diastolic filling time at the time of awakening. This value is used as the criteria for increasing rate before awakening and also for limiting synchronous tracking and rate response. In another version, the pacemaker computes a value of diastolic filling time (DFT) as a function of QT interval, AV interval and RR interval, and modifies pacing rate before and even after awakening to achieve, within predetermined tolerances, the computed value.

The preferred embodiments of the invention are illustrated in terms of utilizing the QT interval as an indirect measure of diastolic filling time. The invention also embraces the use of other data from the QRS-T signal for obtaining data indicative of diastolic filling time, and hence controlling the rate variation during the morning.

BRIEF DESCRIPTION OF THE DRAWINGS

FIG. 4 is a flow diagram of another routine for providing therapy in accordance with this invention.

FIG. 6 is a flow diagram of a routine for storing, organizing and using QRS-T data in determining a measure of minimum diastolic filling time, in accordance with this invention.

DESCRIPTION OF THE PREFERRED EMBODIMENTS

Figure 1:
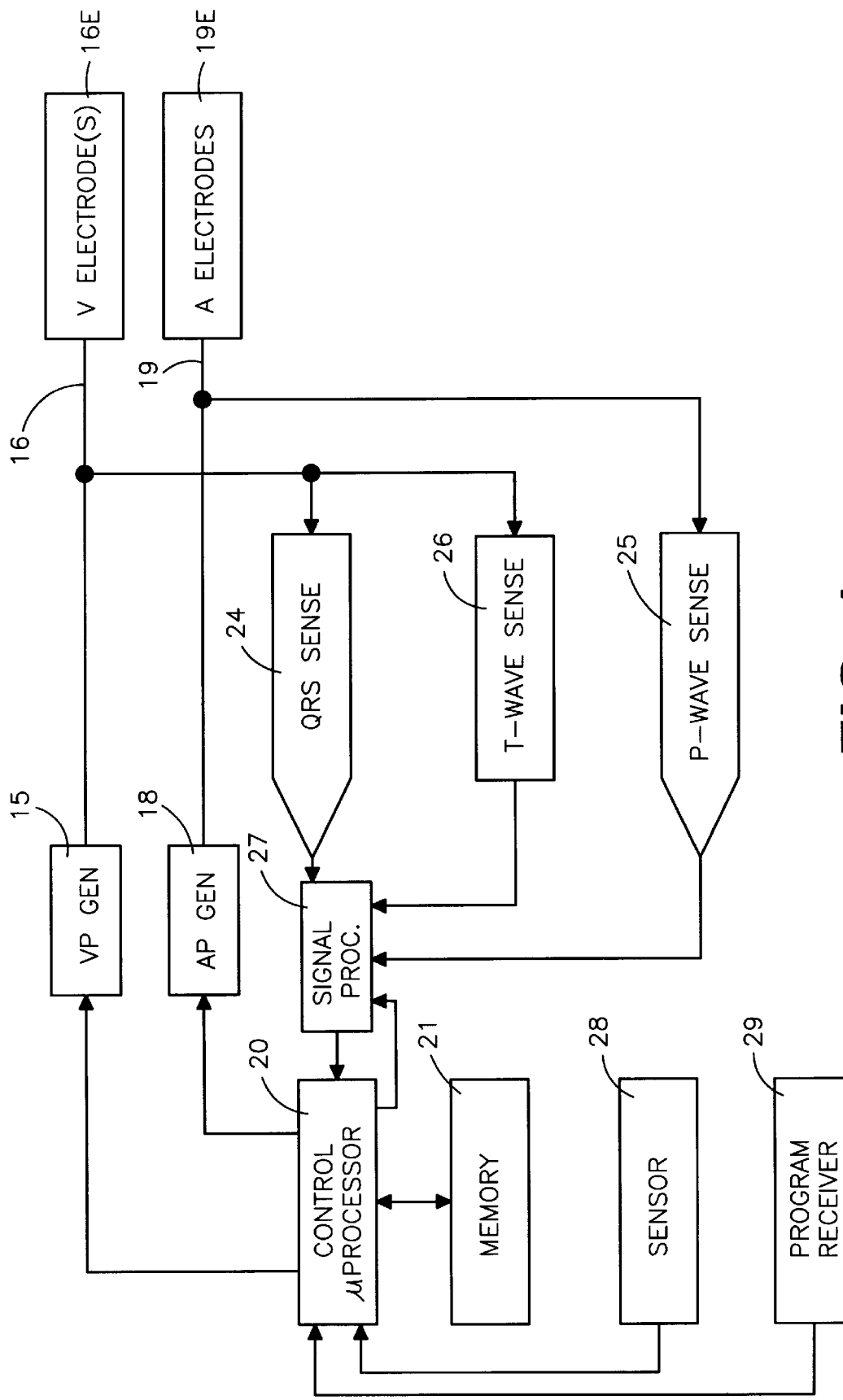
FIG. 1 is a block diagram illustrating the primary components of an exemplary pacemaker embodiment.

Referring now to FIG. 1, there is shown a block diagram of the primary functional components of an illustrative pacemaker system for use in this invention. A VP generator 15 provides pacing pulses, generated under control of block 20, for delivery through lead 16 to one or more ventricular electrodes 16E located in the patient's right ventricle. Likewise, AP generator 18 provides atrial pacing pulses, also generated under control of block 20, for delivery through lead 19 to one or more atrial electrodes 19E located in the patient's right atrium. While not shown, it is understood that the invention is equally applicable to single chamber and to other multi-chamber configurations. Signals sensed by electrodes 16E are connected to QRS Sense circuit 24 which amplifies the signals and provides V-Sense, or VS signals to signal processing block 27. Signals from ventricular electrodes 16E are also passed to T-Wave sense circuit 26, which provides T-Sense signals to block 27. Signals from atrial electrodes 19E are connected to P-Wave sense circuit 25, which outputs A-Sense, or AS signals to block 27.

Block 27 suitably contains dedicated signal processing hardware; and includes an A-D converter for converting the signals into digital form. The QRS and T-wave processing, to obtain a measure of DFT, can be performed in this hardware, or can be done in the microprocessor. The digital signals from block 27 are transferred to block 20 for further processing and/or storage. Block 20 controls the pacemaker functions, e.g., the cyclical functions of setting and timing out escape intervals; receiving sensed signals from the patient's heart and resetting escape intervals based on those signals; and carrying out special functions such as the therapy routines of this invention. Block 20 also suitably is used for calculating start of daytime, and the patient "morning period", as discussed in connection with FIGS. 2A and 2B. Block 20 preferably comprises a microprocessor and associated memory, shown at 21, for storing the required software routines.

The memory 21 suitably includes dedicated RAM and ROM. Control parameters and values can be programmed from an external programmer through program receiver 29, in a known manner. The pacemaker can be programmed to operate in different modes. Sensor 28 may be used to provide a rate responsive parameter, e.g. activity, to be used alone or in combination with another parameter such as QT, in a manner known in the art.

Figure 2A:
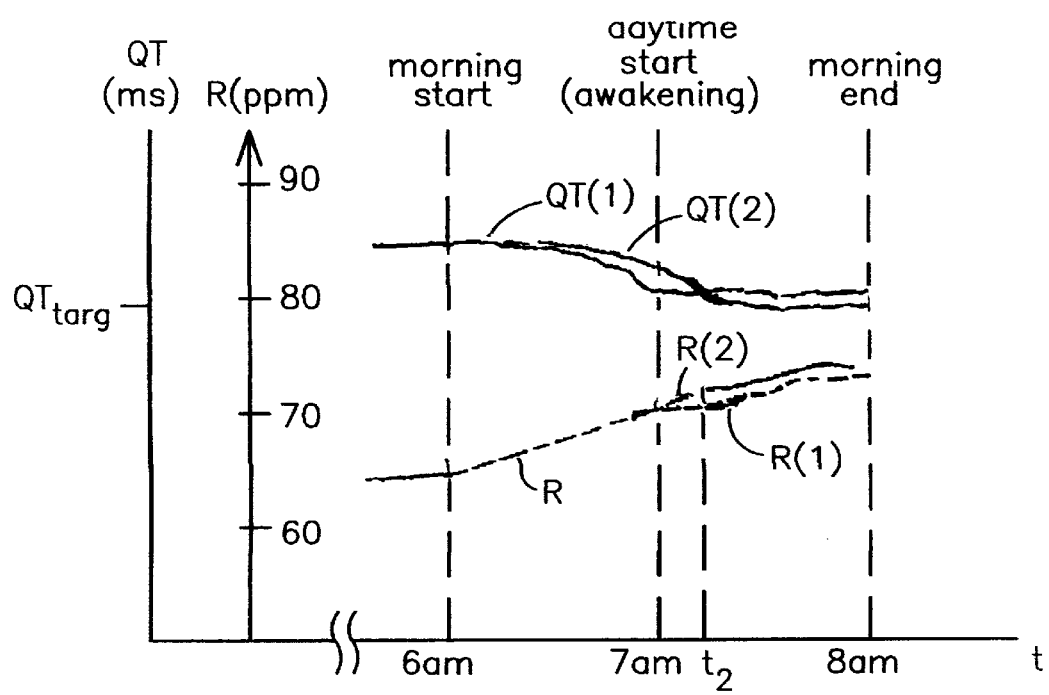
FIG. 2A is a timing diagram illustrating variation of QT interval with pacing rate during a morning period for an embodiment of this invention.

Referring now to FIG. 2A, there is shown a set of curves which illustrate how pacing rate is controlled during the morning period in accordance with this invention, in order to shorten QT interval to a desired value by time of awakening, or at least by the end of the morning period. In this timing diagram, the dashed vertical lines indicate the start of daytime (shown as about 7:00 am); the start of the morning period (illustrated as about 6:00 am); and the end of the morning period (illustrated as about 8:00 am). It is to be understood, however, that end of morning can be set much closer to start of daytime, and indeed can be at the start of daytime, or even before start of daytime. Start of daytime (DT) is determined by any one of a number of known techniques. The simplest way of determining DT is to just program a time, such as 7 am, and use the pacemaker clock to determine start and end of daytime. Of course, diurnal patterns are subject to change, and in a preferred embodiment, DT can be determined daily in the manner as set forth in U.S. patent application Ser. No. 09/179,043, "PACEMAKER SYSTEM WITH DIURNAL PATTERN CONTROLLED OVERDRIVE FOR PREVENTION OF TACHYCARDIA", incorporated herein by reference.

Still referring to FIG. 2A, lines QT(1) and QT(2) illustrate variations of QT interval with time; note that in each case QT int is substantially constant before the start of morning, reflecting a condition of patient sleep. Likewise, the pacing rate R(1) or R(2) is substantially constant until start of the morning period. At start of morning, pacing rate is increased, suitably according to a programmed linear rise. It is important to raise pacing rate slowly, so as to avoid premature awakening of the patient. For example, the rise may be 5 or 10 pulses per minute (ppm) over about one hour. As illustrated in the curve designated QT(1), QT interval responds to the increase in rate illustrated by R(1), and shortens with time. In the example of QT(1), QT interval reaches the $QT_{targ}$ value at about the time of patient awakening, and the therapy routine ends; thereafter, QT and rate vary in a normal fashion, i.e., according to exercise level and/or metabolic demand. In the second example, illustrated by curves QT(2) and R(2), QT int has not shortened to $QT_{targ}$ by awakening, and pacing rate continues to increase slowly until QT drops to $QT_{targ}$ at time $t_2$.

Figure 2B:
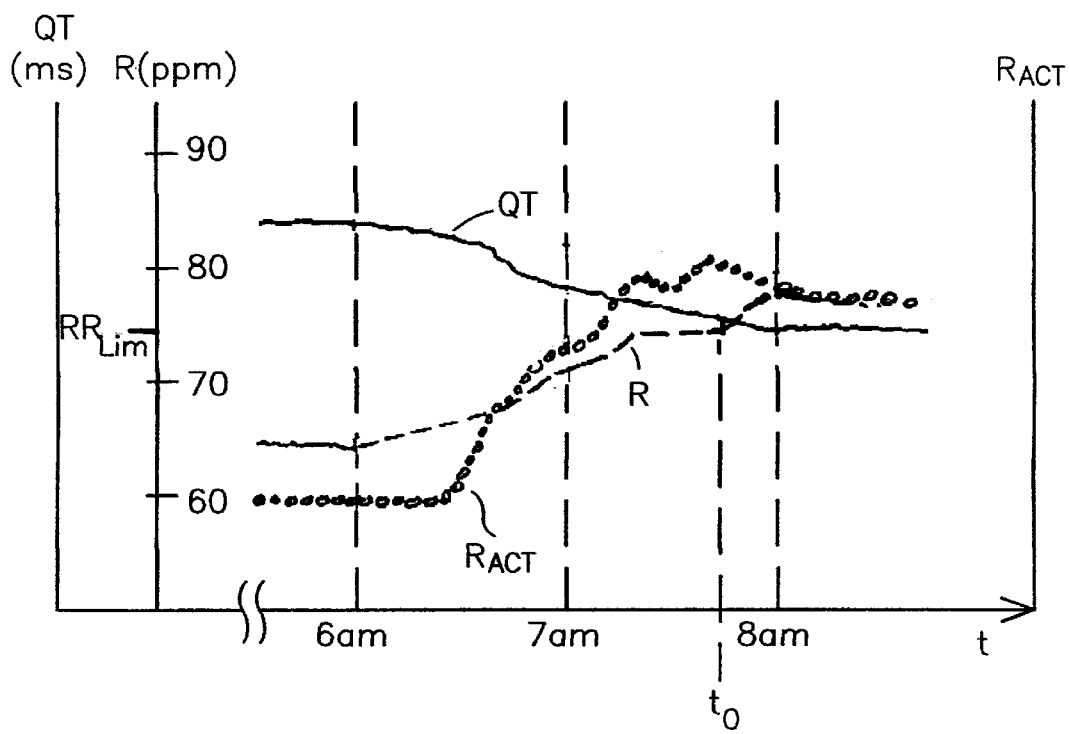
FIG. 2B is a timing diagram showing variations of QT interval and pacing rate during a morning period, and further illustrating actual patient awakening and increase of activity prior to the calculated awakening time.

Referring to FIG. 2B, there is shown another timing diagram, where the pacemaker incorporates an activity sensor for providing a desired Ract pacing rate based on the activity count, in a well known manner. In this illustration, the start of morning occurs before the patient actually gets up; the pacing rate is initially ramped up slowly, the same as in the illustrations of FIG. 2A. Ract, the activity sensor-indicated rate, starts to increase about 15–20 minutes before the pacemaker calculated start of morning, indicating that the patient has in fact arisen before the calculated awakening time. At this time, pacing rate (R) is ramped up at a somewhat greater rate, but not to the full value of Ract. The aim is to react to the patient's premature awakening and shorten the QT interval somewhat more aggressively in order to meet metabolic demand, but not too much. The pacing rate climbs to a limit shown as RRlim, and stays at such rate until QT shortens to an acceptable value, i.e., one that corresponds to RRlim, at time $t_o$. Thereafter, R ramps up to the sensor value, Ract.

Figures 3A, 3B:
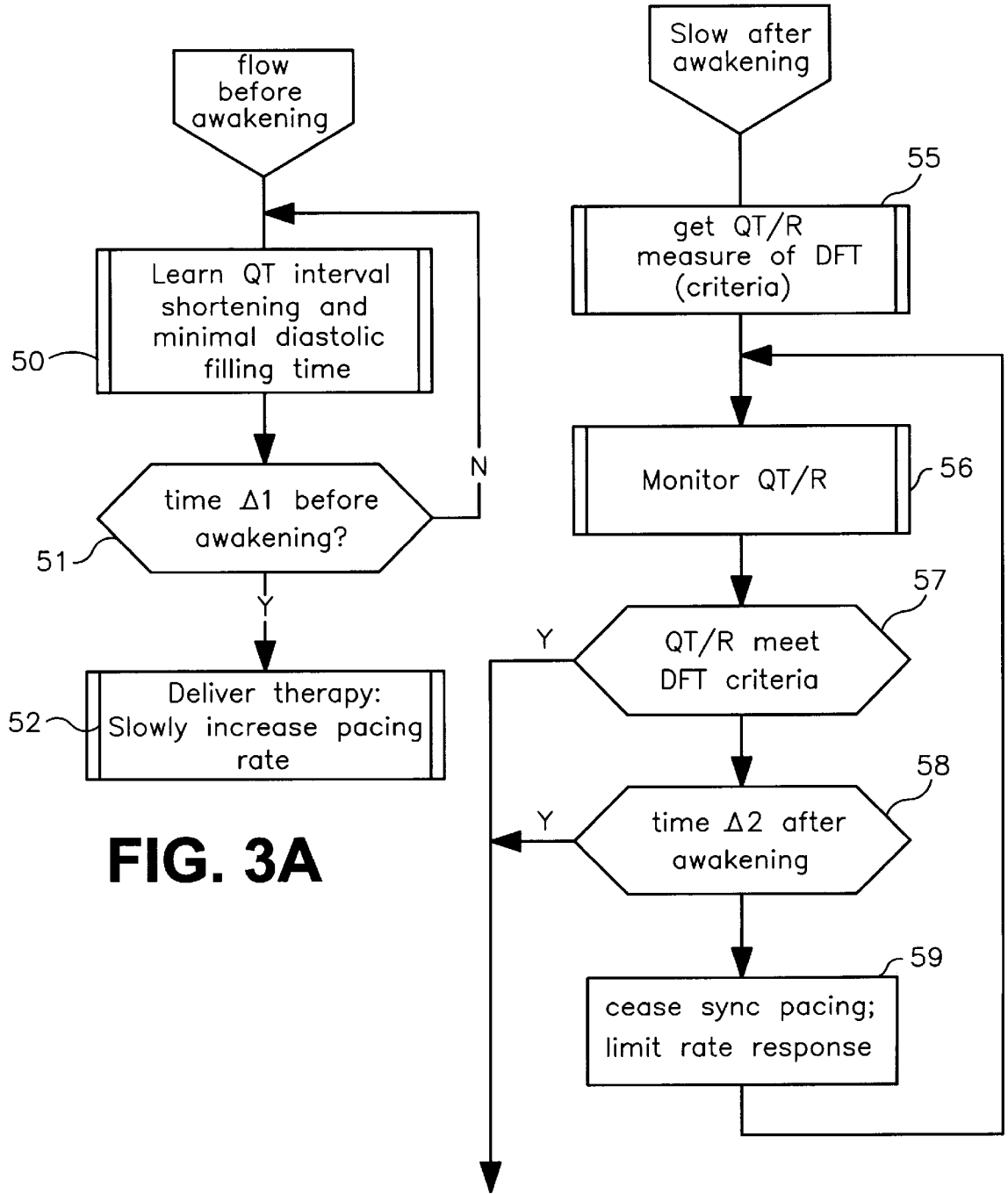
FIG. 3A is a simplified flow diagram of a routine in accordance with this invention, which is carried out prior to patient awakening.
FIG. 3B is a simplified flow diagram of a routine in accordance with this invention, which is carried out after patient awakening.

Referring now to FIGS. 3A and 3B, there are shown flow diagrams illustrating broadly control steps taken in the practice of this invention. In FIG. 3A, the flow before awakening, the pacemaker learns about QT interval shortening and minimal diastolic filling time, as shown at 50. During this routine, the pacemaker updates the target value of QT, or the target value of QT/R, for purposes of establishing a minimal DFT by the time of patient awakening. This process is discussed further in connection with FIG. 6. The pacemaker continuously checks, at 51, to determine whether the morning period has started, i.e., is it delta 1 time before awakening. When morning time commences, at 52 the pacing therapy is delivered, e.g., by slowly increasing pacing rate so as to achieve the target conditions for DFT. When awakening is determined, the pacemaker switches to the flow of FIG. 3B. At 55, the pacemaker gets a measure of DFT, or the DFT criteria. This may be, for example, a value of QT/R for the current rate. This step may involve updating QT interval history, and how it has progressed during the therapy of routine 52. At 56 the pacemaker monitors the current QT slope, or ratio of QT interval to rate. At 57, the pacemaker examines each new slope value, and determines whether it meets the learned criteria, i.e., is QT short enough for the present rate. If no, the pacemaker goes to 58 and determines whether it is yet the end of the morning period, i.e., delta 2 after awakening. If yes, no further therapy is to be delivered, and the routine exits. But if no, then at 59 the pacemaker ceases atrial tracking, and limits pacing rate to a rate below the rate response rate. As used herein, the term "tracking" refers to delivering ventricular pace pulses which are synchronous with atrial senses, i.e., the pacemaker paces the ventricle in tracking relation to the spontaneous atrial beats. This condition is maintained until the DFT criteria are met, or until the morning period is over.

Referring now to FIG. 4, there is illustrated a routine for carrying out a specific preferred embodiment of the invention. When nighttime begins, the start of daytime (DT) is determined at 62. This can be a fixed time, or can be a time that is continually updated during nighttime. At 64, the pacemaker determines when time t is greater than awakening (DT–T1), representing start of the morning period. When this occurs, the routine goes to 66, and examines the QT/R data, and determines therefrom a value of $QT_{targ}$. At 68, pacing rate R is incremented by an amount which is a predetermined function of current pacing rate and current QT. At 70, it is determined whether R is greater than a predetermined limit, $R_{LIM}$. If so, rate should not be increased, and the routine exits. But if no, the routine goes to 72 and determines whether time is still within the morning period, i.e., whether t remains less than DT +T2 (T2 is a programmable value, and can be zero). If no, the therapy is to end, and the routine exits. But if yes, morning is still on-going, the routine goes to 74 and determines whether QT is less than $QT_{targ}$. If yes, then the criteria are met, i.e., QT has been shortened sufficiently, and the routine exits. But if no, then at 76 the pacemaker limits the rate response (effectively disables the rate response feature), and stops tracking spontaneous atrial signals that arrive at a rate above the therapy rate. At 77, the new value of QT/R is stored, and the pacemaker goes to event handling at 78. After the next ventricular event, e.g., delivery of a ventricular pace pulse at the therapy rate R, the loop is reentered at 66. Note that in this arrangement, $QT_{targ}$ does not remain a fixed value, but is calculated to provide an acceptable QT interval corresponding to the current pacing rate.

Figure 5:
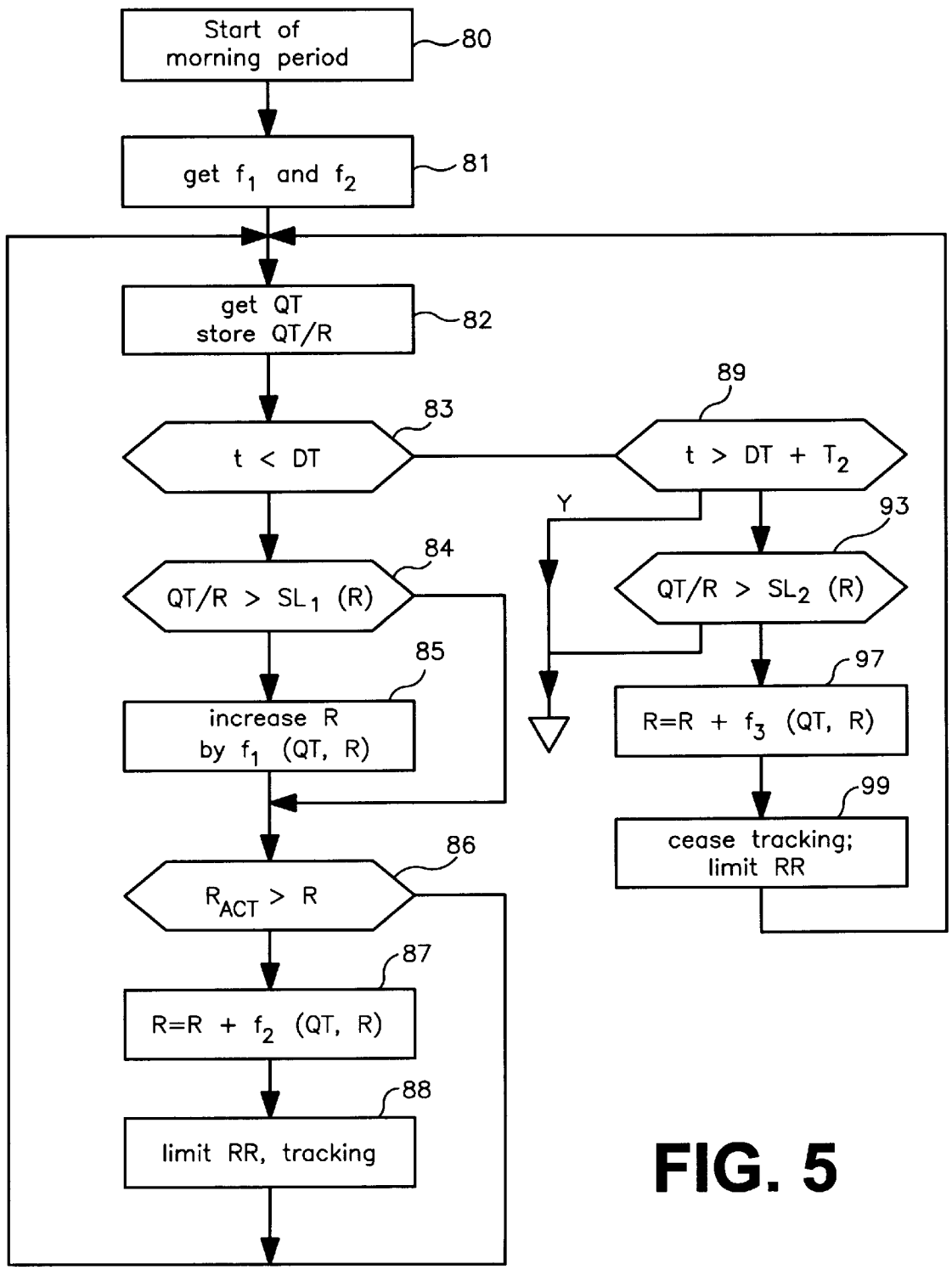
FIG. 5 is another flow diagram of another routine for providing therapy in accordance with this invention.

Referring now to FIG. 5, there is illustrated a flow diagram of another preferred embodiment, wherein the pacemaker incorporates an activity sensor or other indicator of patient cardiac demand. Here, the aim of the routine is to respond to the situation where the patient awakens before the scheduled, or calculated awakening time, and commences activity of a sort which would otherwise call for an increased heart rate. This is a situation which can be potentially dangerous in terms of MI. The patient has arisen before the therapy routine has had a full opportunity to shorten QT interval, based on a normal ramping up of pacing rate, and an adjustment in rate is indicated. Here, two formulas for increasing pacing rate are used, f1 and f2. The first function may be a normal slow, linear increase in pacing rate, as previously illustrated. The second function is a more aggressive increase, to be utilized in the event of a spike in activity before QT has shortened to a desired level. After these functions are obtained at 81, at 82 the routine obtains and stores current values of QT and R, and stores the slope value of QT/R. At 83, it is determined whether it is still prior to DT, or before the awakening time. If not, the routine branches to 89; but if it is still not DT, the routine goes to 84 and determines whether the current slope value is greater than the stored acceptable value for the current rate, $SL_1(R)$. If no, the routine branches to 86. But if not, the routine goes to block 85 and increases R by f1. Then, at 86 it is determined whether $R_{ACT}$ is greater than R, i.e., whether the activity sensor is asking for a higher pacing rate. If yes, then at 87 R is again incremented, this time according to f2. This second function provides for just a small additional increase, so as to provide a compromise between the need to slowly shorten QT and thereby increase diastolic filling time, and the body's request to increase rate so as to meet the demands of the exercise level. At 88, rate response and atrial tracking are limited, i.e., they are disable from controlling pacing rate. The routine continues in this loop until time exceeds DT, as determined at 83. Then, the routine branches to 89, and determines whether morning is over. If yes, the routine exits. If no, then at 93 the current value of QT/R is compared to a second predetermined value, $SL_2(R)$. If this criterion is met, the routine exits. But if not, R is further increased by $f_3$ at 97. At 99, tracking is ceased, and rate response is limited. The pacemaker stays in this state until the end of morning, or until the DFT criteria are met.

Referring now to FIG. 6, there is shown a flow diagram for learning about QT interval shortening and obtaining a measure of diastolic filling time (routine 50 in FIG. 3A). As seen, at block 90, the pacemaker gets the QRS-T signal for the latest cycle, and processes it. At 91, the QT interval is obtained, and at 92 the pacemaker adjusts a QT(R) histogram, to compile data concerning the variation of QT with rate. Such histogram data is suitably further separated as a function of time, to provide comparisons throughout the diurnal cycle. At 94, it is determined whether DFT data is to be obtained, e.g., QRS width, T wave width, etc. If yes, such other data is obtained an processed at 95, and added to other data histogram data at block 96. Then, at 98, an acceptable value of QT/R for morning, or time of awakening, is determined. This flow is exemplary only, and it is to be understood that more sophisticated computations can be performed.

What is claimed is:

1. A pacemaker system for providing pacing therapy to a patient, comprising:

ventricular pace generator means for generating and delivering ventricular pace pulses;

a program for minimizing the risk of MI stored in a computer readable medium in the race generator means;

morning means for determining about when said patient starts a daytime state and for determining a morning time extending from before said start of daytime to at least said start of daytime; and control means for controlling pacing of said patient during said morning time, said control means comprising MI control means for controlling a rate of generation of ventricular pace pulses during the patients morning time in accordance with the program for minimizing the risk of MI.

2. The system as described in claim 1, wherein said morning means comprises start means for determining a start of said morning time as a predetermined time before said start of daytime.

3. The system as described in claim 2, wherein said morning means comprises end means for determining an end of said morning time as a second predetermined time after said start of daytime.

4. The system as described in claim 2, wherein said morning means comprises end means for determining the end of said morning time as when patient activity rises above a predetermined limit.

5. The system as described in claim 1, comprising QT means for determining a patient's QT interval, and wherein said MI control means comprises increase means for increasing a patient's placing rate until the patient QT interval decreases to a predetermined target level.

6. The system as described in claim 5, comprising storing means for storing slope data representative of the relationship of patient QT interval to rate, and target means for determining a QT target level as a function of said slope data.

7. The system as described in claim 5, wherein said increase means comprises algorithm means for increasing pacing rate at a rate of increase so as to decrease QT interval to said target level at least by an end of morning.

8. The system as described in claim 7, wherein said increase means comprises means for increasing pacing rate to a target rate by about said start of daytime.

9. The system as described in claim 1, comprising parameter means for determining a parameter indicative of a desired pacing rate for the patient, rate responsive means for normally controlling the patient pacing rate as a function of said parameter, and limit means for limiting said rate responsive means during the morning time whenever a patient's OT interval has not decreased to a target level.

10. The system as described in claim 1, comprising a dual chamber pacemaker comprising tracking means for delivering ventricular pace pulses in tracked relation to atrial contractions, and limit means for limiting a tracking rate at which atrial contractions are tracked during the morning time as a function of a patient QT interval.

11. A pacemaker system having a MI prevention therapy feature, comprising:

pace means for generating and delivering pace pulses to a patient's ventricle;

rate control means for controlling a rate of said pace pulses;

QT means for determining a measure of the patient's QRS-T signal;

means for determining a morning time period which starts before the patient's nominal awakening time; and said rate control means having first means enabled at the start of said morning time period for increasing pacing rate as a function of said measure.

12. The system as described in claim 11, wherein said QT means comprises means for determining the patient's QT interval, and wherein said rate control means comprises means for raising pacing rate so as to shorten QT interval to a predetermined target value by about the time of patient awakening.

13. The system as described in claim 11, wherein said rate control means comprises means for continuously calculating a ratio of QT interval to pacing rate, and means for raising pacing rate during said morning time period at a rate of increase so as to achieve a predetermined target ratio prior to the end of said morning time period.

14. The system as described in claim 11, further comprising means for determining the patient's QT interval, rate response means for normally controlling pacing rate as a function of at least one predetermined parameter, and limit means for limiting said rate response means to a predetermined rate limit when said QT interval has not shortened to a predetermined QT target value during said morning time period.

15. A pacing system, comprising:

pace means for generating pacing pulses at a controllable pacing rate and for delivering said pacing pulses to a patient's ventricle;

sensing means for sensing QRS-T signals from said patient's heart;

first means for setting QRS-T criteria indicative of patient diastolic filling time;

second means for determining from said sensed QRS-T signals whether said QRS-T criteria are met;

response means operative when said QRS-T criteria are not met for controlling said pacing rate so as to meet said QRS-T criteria;

atrial means for sensing atrial signals;

tracking means for controlling said pace means to deliver pace pulse to the patient's ventricle in synchronous relation to sensed atrial signals, wherein said response means comprises disable means for disabling the operation of said tracking means;

rate responsive means for controlling said pacing rate as a function of a patient metabolic demand, wherein said disabling means further comprises means for disabling said rate responsive means from controlling pacing rate;

morning means for determining a start time before the patient's normal awakening; and therapy means for controlling said pace means to generate and deliver pace pulses to said patient at an increasing rate, and enable means for enabling said therapy means at said start time.

16. The system as described in claim 15, further comprising means for determining the patient's intrinsic heart rate, and wherein said therapy means comprises means for increasing the pacing rate to a rate greater than said intrinsic rate.

* * * * *

UNITED STATES PATENT AND TRADEMARK OFFICE
CERTIFICATE OF CORRECTION

PATENT NO. : 6,238,422 B1
DATED : May 29, 2001
INVENTOR(S) : Van Oort

It is certified that error appears in the above-identified patent and that said Letters Patent is hereby corrected as shown below:

<u>Column 7,</u>
Line 12, change "race" to -- pace --.
Line 21, change "patients" to -- patient's --.
Line 38, change "placing" to -- pacing --.

Signed and Sealed this

Eighteenth Day of March, 2003

JAMES E. ROGAN
*Director of the United States Patent and Trademark Office*